US008865857B2

(12) United States Patent
Ladet et al.

(10) Patent No.: US 8,865,857 B2
(45) Date of Patent: Oct. 21, 2014

(54) MEDICAL DEVICE WITH PREDEFINED ACTIVATED CELLULAR INTEGRATION

(75) Inventors: Sébastien Ladet, Caluire et Cuire (FR); Philippe Gravagna, Irigny (FR)

(73) Assignee: Sofradim Production (FR)

( * ) Notice: Subject to any disclaimer, the term of this patent is extended or adjusted under 35 U.S.C. 154(b) by 0 days.

(21) Appl. No.: 13/807,981

(22) PCT Filed: Jun. 30, 2011

(86) PCT No.: PCT/IB2011/002260
§ 371 (c)(1),
(2), (4) Date: Feb. 15, 2013

(87) PCT Pub. No.: WO2012/001532
PCT Pub. Date: Jan. 5, 2012

(65) Prior Publication Data
US 2013/0143976 A1    Jun. 6, 2013

Related U.S. Application Data

(60) Provisional application No. 61/360,691, filed on Jul. 1, 2010.

(51) Int. Cl.
*C08G 63/00* (2006.01)
*C08G 63/02* (2006.01)

(52) U.S. Cl.
USPC ........... 528/196; 530/330; 530/331; 528/198; 604/103.2; 604/506; 604/509; 604/529

(58) Field of Classification Search
USPC .................................. 521/421; 530/330, 331
See application file for complete search history.

(56) References Cited

U.S. PATENT DOCUMENTS

| | | | |
|---|---|---|---|
| 3,494,359 A | 2/1970 | Zackheim | |
| 3,767,085 A | 10/1973 | Cannon et al. | |
| 4,326,532 A | 4/1982 | Hammar | |
| 4,359,049 A | 11/1982 | Redl et al. | |
| 4,464,321 A | 8/1984 | Pittalis et al. | |
| 4,538,920 A | 9/1985 | Drake | |
| 4,753,536 A | 6/1988 | Spehar et al. | |
| 4,839,345 A | 6/1989 | Doi et al. | |
| 4,857,403 A | 8/1989 | De Lucca et al. | |
| 4,880,662 A | 11/1989 | Habrich et al. | |
| 4,898,580 A | 2/1990 | Crowley | |
| 4,915,695 A | 4/1990 | Koobs | |
| 5,021,207 A | 6/1991 | De Lucca et al. | |
| 5,104,375 A | 4/1992 | Wolf et al. | |
| 5,372,585 A | 12/1994 | Tiefenbrun et al. | |
| 5,455,308 A | 10/1995 | Bastiaansen | |
| 5,562,946 A | 10/1996 | Fofonoff et al. | |
| 5,578,662 A | 11/1996 | Bennett et al. | |
| 5,582,955 A | 12/1996 | Keana et al. | |
| 5,612,050 A | 3/1997 | Rowe et al. | |
| 5,685,846 A | 11/1997 | Michaels, Jr. | |
| 5,804,318 A | 9/1998 | Pinchuk et al. | |
| 5,911,942 A | 6/1999 | Fofonoff et al. |
| 5,916,585 A | 6/1999 | Cook et al. |
| 5,935,437 A | 8/1999 | Whitmore |
| 5,971,953 A | 10/1999 | Bachynsky |
| 6,099,563 A | 8/2000 | Zhong |
| 6,107,365 A | 8/2000 | Bertozzi et al. |
| 6,107,453 A | 8/2000 | Zuccato et al. |
| 6,312,725 B1 | 11/2001 | Wallace et al. |
| 6,342,591 B1 | 1/2002 | Zamora et al. |
| 6,406,455 B1 | 6/2002 | Willis et al. |
| 6,451,032 B1 | 9/2002 | Ory et al. |
| 6,534,611 B1 | 3/2003 | Darling et al. |
| 6,552,103 B1 | 4/2003 | Bertozzi et al. |
| 6,570,040 B2 | 5/2003 | Saxon et al. |
| 6,576,000 B2 | 6/2003 | Carrison |
| 6,624,245 B2 | 9/2003 | Wallace et al. |
| 6,805,876 B2 | 10/2004 | Leong et al. |
| 6,881,766 B2 | 4/2005 | Hain |
| 6,958,212 B1 | 10/2005 | Hubbell et al. |
| 7,012,126 B2 | 3/2006 | Matsuda et al. |
| 7,105,629 B2 | 9/2006 | Matsuda et al. |
| 7,122,703 B2 | 10/2006 | Saxon et al. |
| 7,144,976 B2 | 12/2006 | Matsuda et al. |
| 7,172,877 B2 | 2/2007 | Ting |
| 7,247,692 B2 | 7/2007 | Laredo |
| 7,294,357 B2 | 11/2007 | Roby |
| 7,371,719 B2 | 5/2008 | Stupp et al. |

(Continued)

FOREIGN PATENT DOCUMENTS

| | | |
|---|---|---|
| BE | 1008260 A6 | 2/1996 |
| EP | 0077098 A2 | 4/1983 |

(Continued)

OTHER PUBLICATIONS

Q. Shi, et al., "The Immobilization of Proteins on Biodegradable Polymer Fibers via Click Chemistry", Biomaterials, 29, (2008), pp. 1118-1126.
Jérôme, et al., "Recent Advances in the Synthesis of Aliphatic Polyesters Ring-Opening Polymerization", Advanced Drug Delivery Reviews, 60, (2008), pp. 1056-1076.
Zhang, et al., "2-Azido-2-deoxycellulose: Synthesis and 1, 3-Dipolar Cycloaddition", Helvetica Chimica Acta, vol. 91, pp. 608-617 (2008); (Abstract Only).
R. Riva, et al., "Contribution of "Click Chemistry" to the Synthesis of Antimicrobial Aliphatic Copolyester", Polymer 49, (2008), pp. 2023-2028.
Baskin, et al., "Copper Free Click Chemistry for Dynamic In Vivo Imaging", PNAS, vol. 104, No. 43, (Oct. 23, 2007), pp. 16793-16797.
Codelli, et al., "Second Generation Difluorinated Cyclooctynes for Copper-Free Click Chemistry", J. Am. Chem. Soc., vol. 130, No. 34, (2008), pp. 11486-11493.
Sletten and Bertozzi, "A Hydrophilic Azacyclooctyne for Cu-free Click Chemistry", Org. Lett. (2008) 10(14), pp. 3097-3099.

(Continued)

*Primary Examiner* — Terressa Boykin

(57) ABSTRACT

A medical device includes a substrate having at least a portion thereof functionalized with at least one reactive member and a chemotactic agent functionalized with at least one complementary reactive member. The at least one reactive member and the at least one complementary reactive member are covalently bonded, adhering the chemotactic agent to the substrate.

20 Claims, 1 Drawing Sheet

(56) References Cited

U.S. PATENT DOCUMENTS

| | | |
|---|---|---|
| 7,375,234 B2 | 5/2008 | Sharpless et al. |
| 7,560,588 B2 | 7/2009 | Breitenkamp et al. |
| 7,618,944 B2 | 11/2009 | Breitenkamp et al. |
| 7,638,558 B2 | 12/2009 | Breitenkamp et al. |
| 7,650,588 B2 | 1/2010 | Ivansen |
| 7,667,012 B2 | 2/2010 | Saxon et al. |
| 7,795,355 B2 | 9/2010 | Matyjaszewski et al. |
| 7,807,619 B2 | 10/2010 | Bertozzi et al. |
| 7,981,444 B2 | 7/2011 | Tomalia et al. |
| 7,985,424 B2 | 7/2011 | Tomalia et al. |
| 8,034,396 B2 | 10/2011 | Kapiamba et al. |
| 2002/0016003 A1 | 2/2002 | Saxon et al. |
| 2002/0161170 A1 | 10/2002 | Matsuda et al. |
| 2002/0169275 A1 | 11/2002 | Matsuda et al. |
| 2002/0173616 A1 | 11/2002 | Matsuda et al. |
| 2003/0100086 A1 | 5/2003 | Yao et al. |
| 2003/0135238 A1 | 7/2003 | Milbocker |
| 2003/0162903 A1 | 8/2003 | Day |
| 2003/0199084 A1 | 10/2003 | Saxon et al. |
| 2003/0205454 A1 | 11/2003 | Hlavinka et al. |
| 2004/0170752 A1 | 9/2004 | Luthra et al. |
| 2004/0185053 A1 | 9/2004 | Govindan |
| 2004/0209317 A1 | 10/2004 | Ting |
| 2004/0249438 A1 | 12/2004 | Lefranc et al. |
| 2005/0032081 A1 | 2/2005 | Ju et al. |
| 2005/0038472 A1 | 2/2005 | Furst |
| 2005/0148032 A1 | 7/2005 | Saxon et al. |
| 2005/0222427 A1 | 10/2005 | Sharpless et al. |
| 2005/0233389 A1 | 10/2005 | Ting et al. |
| 2005/0244453 A1 | 11/2005 | Stucke et al. |
| 2006/0018948 A1 | 1/2006 | Guire et al. |
| 2006/0036022 A1 | 2/2006 | Callaghan et al. |
| 2006/0050262 A1 | 3/2006 | Poon et al. |
| 2006/0085033 A1 | 4/2006 | Criscuolo et al. |
| 2006/0108393 A1 | 5/2006 | Heinrich et al. |
| 2006/0110782 A1 | 5/2006 | Bertozzi et al. |
| 2006/0142404 A1 | 6/2006 | Berge et al. |
| 2006/0147963 A1 | 7/2006 | Barone et al. |
| 2006/0189944 A1 | 8/2006 | Campbell et al. |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0240092 A1 | 10/2006 | Breitenkamp et al. |
| 2006/0276658 A1 | 12/2006 | Saxon et al. |
| 2007/0005020 A1 | 1/2007 | Laveault |
| 2007/0020620 A1 | 1/2007 | Finn et al. |
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0140966 A1 | 6/2007 | Chang et al. |
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0212267 A1 | 9/2007 | Organ et al. |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0021486 A1 | 1/2008 | Oyola et al. |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0103564 A1 | 5/2008 | Burkinshaw et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2008/0317861 A1 | 12/2008 | Guan |
| 2009/0012457 A1 | 1/2009 | Childers et al. |
| 2009/0018646 A1 | 1/2009 | Zhao |
| 2009/0027603 A1 | 1/2009 | Samulski et al. |
| 2009/0038701 A1 | 2/2009 | Delmotte |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0099108 A1 | 4/2009 | Jones |
| 2009/0124534 A1 | 5/2009 | Reineke et al. |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0203131 A1 | 8/2009 | Reineke et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2009/0325292 A1 | 12/2009 | Baker et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0098640 A1 | 4/2010 | Cohen et al. |
| 2010/0104589 A1 | 4/2010 | Govindan et al. |
| 2010/0121022 A1 | 5/2010 | Musa et al. |
| 2010/0159508 A1 | 6/2010 | Yang et al. |
| 2010/0247433 A1 | 9/2010 | Tirrell et al. |
| 2010/0286405 A1 | 11/2010 | Fokin et al. |
| 2010/0291171 A1 | 11/2010 | Crescenzi et al. |
| 2010/0303754 A1 | 12/2010 | Turpin et al. |
| 2011/0008251 A1 | 1/2011 | Chang et al. |
| 2011/0052696 A1 | 3/2011 | Hult et al. |
| 2011/0060107 A1 | 3/2011 | Matyjaszewski et al. |
| 2011/0143435 A1 | 6/2011 | Stayton et al. |
| 2011/0177156 A1 | 7/2011 | Szoka, Jr. et al. |
| 2011/0183417 A1 | 7/2011 | Reineke |
| 2011/0213123 A1 | 9/2011 | Bertozzi et al. |
| 2011/0305898 A1* | 12/2011 | Zhang et al. .......... 428/336 |

FOREIGN PATENT DOCUMENTS

| | | |
|---|---|---|
| EP | 0328050 A2 | 8/1989 |
| EP | 0490854 B1 | 9/1996 |
| EP | 1790702 A1 | 5/2007 |

(56) References Cited

FOREIGN PATENT DOCUMENTS

| | | |
|---|---|---|
| EP | 1795563 A1 | 6/2007 |
| EP | 2014308 A2 | 1/2009 |
| EP | 2090592 A1 | 8/2009 |
| WO | WO 99/11692 A1 | 3/1999 |
| WO | WO 99/28354 A1 | 6/1999 |
| WO | WO 00/62827 A2 | 10/2000 |
| WO | WO 01/68565 A2 | 9/2001 |
| WO | WO 03/101972 A1 | 12/2003 |
| WO | WO 2004/054622 A1 | 7/2004 |
| WO | WO 2005/062854 A2 | 7/2005 |
| WO | WO 2005/079217 A2 | 9/2005 |
| WO | WO 2005/084180 A2 | 9/2005 |
| WO | WO 2005/084367 A2 | 9/2005 |
| WO | WO 2005/087818 A1 | 9/2005 |
| WO | WO 2005/113605 A1 | 12/2005 |
| WO | WO 2006/005046 A2 | 1/2006 |
| WO | WO 2006/012569 A1 | 2/2006 |
| WO | WO 2006/050262 A2 | 5/2006 |
| WO | WO 2006/065266 A2 | 6/2006 |
| WO | WO 2006/084202 A2 | 8/2006 |
| WO | WO 2006/091894 A2 | 8/2006 |
| WO | WO 2006/107617 A2 | 10/2006 |
| WO | WO 2006/107786 A2 | 10/2006 |
| WO | WO 2006/107903 A2 | 10/2006 |
| WO | WO 2007/002109 A2 | 1/2007 |
| WO | WO 2007/003054 A1 | 1/2007 |
| WO | WO 2007/011696 A2 | 1/2007 |
| WO | WO 2007/011967 A2 | 1/2007 |
| WO | WO 2007/021762 A2 | 2/2007 |
| WO | WO 2007/021763 A2 | 2/2007 |
| WO | WO 2007/022070 A2 | 2/2007 |
| WO | WO 2007/027493 A2 | 3/2007 |
| WO | WO 2007/035296 A2 | 3/2007 |
| WO | WO 2007/039858 A2 | 4/2007 |
| WO | WO 2007/041394 A2 | 4/2007 |
| WO | WO 2007/041451 A2 | 4/2007 |
| WO | WO 2007/046893 A2 | 4/2007 |
| WO | WO 2007/047301 A2 | 4/2007 |
| WO | WO 2007/047609 A2 | 4/2007 |
| WO | WO 2007/047668 A2 | 4/2007 |
| WO | WO 2007/047796 A2 | 4/2007 |
| WO | WO 2007/056561 A2 | 5/2007 |
| WO | WO 2007/075270 A2 | 7/2007 |
| WO | WO 2007/081876 A2 | 7/2007 |
| WO | WO 2007/104948 A2 | 9/2007 |
| WO | WO 2007/112193 A2 | 10/2007 |
| WO | WO 2007/121055 A1 | 10/2007 |
| WO | WO 2007/125429 A2 | 11/2007 |
| WO | WO 2007/127473 A2 | 11/2007 |
| WO | WO 2007/132000 A1 | 11/2007 |
| WO | WO 2007/132005 A2 | 11/2007 |
| WO | WO 2008/004988 A1 | 1/2008 |
| WO | WO 2008/006097 A2 | 1/2008 |
| WO | WO 2008/008483 A1 | 1/2008 |
| WO | WO 2008/011335 A2 | 1/2008 |
| WO | WO 2008/013618 A1 | 1/2008 |
| WO | WO 2008/016371 A2 | 2/2008 |
| WO | WO 2008/017029 A2 | 2/2008 |
| WO | WO 2008/019450 A1 | 2/2008 |
| WO | WO 2008/024435 A2 | 2/2008 |
| WO | WO 2008/031525 A1 | 3/2008 |
| WO | WO 2008/036350 A2 | 3/2008 |
| WO | WO 2008/047057 A1 | 4/2008 |
| WO | WO 2008/048288 A2 | 4/2008 |
| WO | WO 2008/048733 A1 | 4/2008 |
| WO | WO 2008/060333 A1 | 5/2008 |
| WO | WO 2008/075955 A2 | 6/2008 |
| WO | WO 2008/077406 A2 | 7/2008 |
| WO | WO 2008/088658 A2 | 7/2008 |
| WO | WO 2008/091349 A1 | 7/2008 |
| WO | WO 2008/094254 A2 | 8/2008 |
| WO | WO 2008/101024 A2 | 8/2008 |
| WO | WO 2008/101069 A1 | 8/2008 |
| WO | WO 2008/105773 A2 | 9/2008 |
| WO | WO 2008/105902 A2 | 9/2008 |
| WO | WO 2008/106657 A2 | 9/2008 |
| WO | WO 2008/108736 A1 | 9/2008 |
| WO | WO 2008/115694 A2 | 9/2008 |
| WO | WO 2008/120016 A1 | 10/2008 |
| WO | WO 2008/121375 A2 | 10/2008 |
| WO | WO 2009/029242 A1 | 3/2009 |
| WO | WO 2009/064696 A1 | 5/2009 |
| WO | WO 2009/136853 A1 | 11/2009 |
| WO | WO 2009/140429 A2 | 11/2009 |
| WO | 2010095044 A2 | 8/2010 |
| WO | 2010095046 A2 | 8/2010 |
| WO | 2010095052 A2 | 8/2010 |
| WO | 2010095056 A2 | 8/2010 |
| WO | 2010095057 A1 | 8/2010 |
| WO | 2010095058 A2 | 8/2010 |
| WO | WO 2010/095049 A1 | 8/2010 |

OTHER PUBLICATIONS

Cazalis, et al., "C-Terminal Site-Specific PEGylation of a Truncated Thrombomodulin Mutant with Retention of Full Bioactivity", Bioconjugate Chem., (2004), 15, pp. 1005-1009.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

Le Dévédec, et al., "Separation of Chitosan Oligomers by Immobilized Metal Affinity Chromatography", Journal of Chromatography A., 2008, 1194(2), pp. 165-171.

Hartgerink, et al., "Peptide-amphiphile Nanofibers: A Versatile Scaffold for the Preparation of Self Assembling Materials", PNAS, 2002; 99(2), pp. 5133-5138.

Van Berkel, et al., "Metal-Free Triazole Formation as a Tool for Bioconjugation" Chem Bio Chem, 8, (2007), pp. 1504-1508.

Nottelet, et al., Snythesis of an X-ray opaque biodegradable copolyester by chemical modification of poly (ε-caprolactone) Biomaterials, 27, (2006), pp. 4943-4954.

Smith, et al., "Synthesis and Convenient Functionalization of Azide-labeled Diacyglycerol. Analogues for Modular Access to Biologically Active Lipid Probes", Bioconjugate Chem, 19(9), (2008). pp. 1855-1863; (Abstract Only).

Skierka, et al., "The Influence of Different Acids and Pepsin on the Extractability of Collagen From the Skin of Baltic Cod (*Gadus Morhua*)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.

Witczak et al., "A Click Chemistry Approach to Glycomimetics: Michael addition of 2,3,4,6-tetra-*O*-acety1-1-thio-β-D-glucopyranose to 4-deoxy-1,2-*O*-isopropylident-L-*glycero*-pent-4-enopyranos-3-ulose-a convenient route to novel 4-deoxy-(1→5)-5-*C*-thiodisaccharides", Carbohydrate Research, 342, (2007), 1929-1933.

Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461; (Abstract Only).

Srinivasachari, et al., "Versatile Supramolecular pDNA Vehicles via "Click Polymerization" of β-cyclodextrin with oligoethyleneamines", Biomaterials, 30, (2009), pp. 928-938.

Arora, et al., "A Novel domino-click approach for the synthesis of sugar based unsymmetrical bis-1,2,3-triazoles", Carbohydrate Research, 343, (2008), 139-144.

(56) References Cited

OTHER PUBLICATIONS

Chen, et al., "Synthesis of a $C_3$-symmetric (1→6)-*N*-acetyl-β-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045; (Abstract Only).

Srinivasachari, et. al., "Effects of Trehalose Click Polymer Length on pDNA Complex Stability and Delivery Efficacy", Biomaterials, 28, (2007), pp. 2885-2898.

Godeau, et al., Lipid-Conjugated Oligonucleotides via "Click Chemistry" Efficiently Inhibit Hepatitis C Virus Translation, J. med. Chem., 2008, 51(15), pp. 2374-4376; (Abstract Only).

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via *i* to *i*+4 Intramolecular Side-chain to Side-chain Azide-Alkyne 1,3-Dipolar Cycloaddition" J. Org. Chem., 2008, 73 (15), pp. 5663-5614; (Abstract Only).

Dijk, et al., "Synthesis of Peptide-Based Polymers by Microwave-Assisted Cycloaddition Backbone Polymerization, "Biomacro molecules, 2007, 8(2), pp. 327-330; (Abstract Only).

Köster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332; (Abstract Only).

Dijk, et al., "Synthesis and Characterizition of Biodegradable Peptide-Baed Polymers Prepared by Microwave-Assisted Click Chemistry", Biomacromolecules, 2008, 9(10), pp. 2834-2843; (Abstract Only).

Jiang, et al., "Amphiphilic PEG/alkyl-grafted comb polylactides", J. Polymer Science Part B: Polymer Physics, 45(22), 2007, pp. 5227-5236; (Abstract Only).

Ochs, et al., "Low-Fouling, Biofunctionalized, and Biodegradable Click Capsules"; Biomacromolecules, 2008, 9(12), pp. 3389-3396; (Abstract Only).

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

Krouit, et al., "Cellulose surface grafting with polycaprolactone by heterogeneous click-chemistry", European Polymer Journal 44, Dec. 2008, pp. 4074-4081; (Abstract Only).

Nandivada, et al. "Reactive polymer coatings that 'Click'", Angewandte Chemie, International Edition 45, Apr. 2006, pp. 3360-3363; (Abstract Only).

Ossipov and Hilborn, Poly(vinyl alcohol)-Based Hydrogels Formed by "Click Chemistry", Macromelecules 2006, 39, pp. 1709-1718.

Binder and Sachsenhofer, "Click Chemistry in Polymer and Materials Science", Macromolecular Rapid Commun. 2007; 28, pp. 15-54.

International Search Report, Application No. PCT/IB2011/002260 dated Jan. 16, 2012.

\* cited by examiner

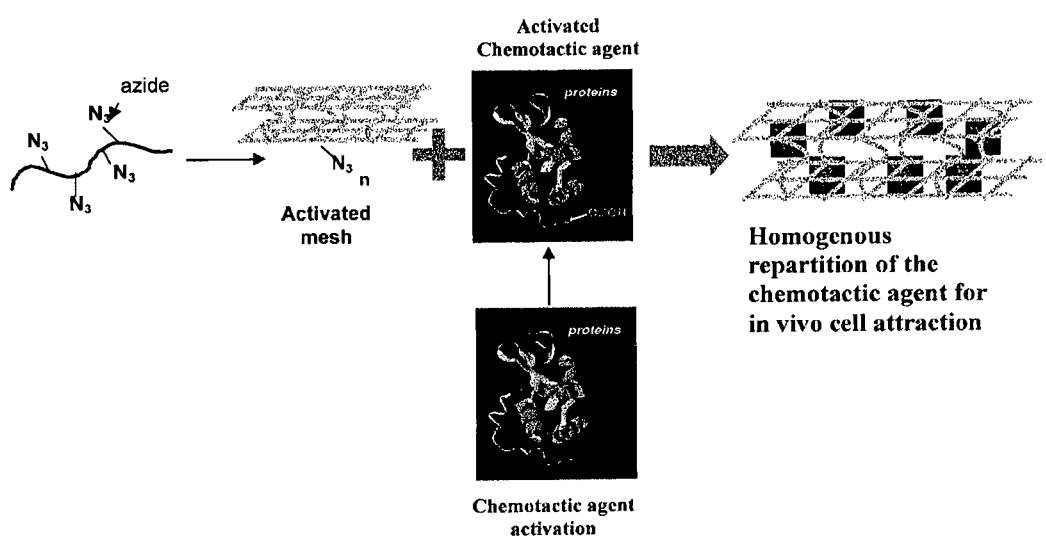

MEDICAL DEVICE WITH PREDEFINED ACTIVATED CELLULAR INTEGRATION

CROSS-REFERENCE TO RELATED APPLICATIONS

This application is a U.S. National Stage Application filed under 35 U.S.C. §371(a) of International Application No. PCT/IB2011/002260 filed Jun. 30, 2011, which claims the benefit of and priority to U.S. Provisional Patent Application Ser. No. 61/360,691 filed Jul. 1, 2010, the entire contents of which are incorporated by reference herein.

BACKGROUND

1. Technical Field

The present disclosure relates to methods of making implantable medical devices having a coating that produces a specific chemotactic response.

2. Background of Related Art

Techniques for repairing damaged or diseased tissue are widespread in medicine. Wound closure devices such as sutures, staples and other repair devices such as mesh or patch reinforcements are frequently used for repair. Surgical adhesives have been used to augment and, in some cases, replace sutures and staples in wound closure. For example, in the case of hernias, techniques involving the use of a mesh or patch to reinforce the abdominal wall are being used. The mesh or patch can generally be held in place by suturing or stapling to the surrounding tissue. Unfortunately, the use of such sutures or staples may increase the patient's discomfort and, in certain instances, there may be a risk of weakening thin or delicate tissue where they are attached. Certain techniques involve placing a mesh or patch against the repair site without suturing or stapling, e.g., allowing the pressure of the peritoneum to hold the patch against the posterior side of the abdominal wall. However, fixation of the mesh or patch is generally preferred in order to avoid folding, shrinkage, and migration of the mesh or patch. Surgical adhesives such as cyanoacrylates and fibrin glues have been used as fixatives in lieu of, or in addition to, suturing or stapling the mesh or patch. However, fibrin adhesives can be difficult to prepare and store. Cyanoacrylates may cause irritation at the point of application and may not provide a sufficient degree of elasticity. In addition, surgical adhesives can tend to form a physical barrier between the item or items being attached to biological tissue, thus interfering with tissue ingrowth into the item when ingrowth is desired.

Click chemistry is a popular term for reliable reactions that make it possible for certain chemical building blocks to "click" together and form an irreversible linkage. Since its recent introduction, click chemistry has been used for ligation in biological and medical technology. In the case of azide-alkyne click chemistry, the reactions may be catalyzed or uncatalyzed, as illustrated in US Patent Publication. No. 2005/0222427 and PCT P2006/050262, respectively. Copper-free click chemistry was recently developed by Bertozzi and colleagues using difluorinated cyclooctyne or DIM, that reacts with azides rapidly at physiological temperatures without the need for a toxic catalyst as disclosed in Baskin et al., "Copper Free Click Chemistry for Dynamic In Vivo Imaging," PNAS, vol. 104, no. 43, 16793-16797 (Oct. 23, 2007). The critical reagent, a substituted cyclooctyne, possesses ring strain and electron-withdrawing fluorine substituents that together promote a [3+2] dipolar cycloaddition with azides as disclosed in US Patent Publication No. 2006/0110782 and "Codelli et al., Second Generation Difluorinated Cyclooctynes for Copper-Free Click Chemistry," J. Am. Chem. Soc., vol. 130, no. 34, 11486-11493 (2008). Another suitable cyclooctyne is 6,7-dimethoxyazacyclooct-4-yne (DIMAC) as disclosed in Sletton and Bertozzi, "A Hydrophilic Azacyclooctyne for Cu-free Click Chemistry," Org. Lett. (2008) 10 (14), 3097-3099. Other click chemistry reactions include Diels-Alder reactions, thiol-alkene reactions, and maleimide-thiol reactions.

Implantable medical devices are formed from a variety of different biodegradable and non-biodegradable materials. Non-biodegradable devices offer increased strength and support, however, some medical devices do not fully integrate within the tissue due poor cell seeding within the devices. Accordingly, it would be beneficial to provide a medical device which includes a coating that encourages cell attachment thereto.

SUMMARY

Implantable medical devices are described herein which include a substrate and a coating disposed on a surface thereof. The coating includes one or more chemotactic agents, which are useful for attracting cells, modulating cell attachment, guiding cellular ingrowth, including cell proliferation and/or differentiation.

In particular, the present disclosure relates to tissue-engineered medical devices, and to cell therapy which restores, maintains and/or improves tissue functions. Such devices may include a three-dimensional substrate (e.g., scaffold) that acts as a substrate for cell attachment and recruitment. Cells seeded in the substrate recreate the in vivo microenvironment, thereby facilitating cell-to-cell interactions and expression of differentiated functions. To construct such a complex structure, the efficiency of the cell seeding process can be important to the overall performance of the scaffold construct. Moreover during in vivo implantation the optimization of the scaffold implant that can specifically interact with cells within the device is also envisioned. The efficiency of the cell seeding process or cells colonization in vivo may also be adjusted by the porosity, the nature and material composition of the scaffold itself.

The present disclosure relates to the functionalization of the materials used in the preparation of scaffolds for regenerative medicine to maximize cellular integration. This may be accomplished via chemical reactions, including but not limited to, "click chemistry" involving azide or alkyne groups. The chemical reaction of click chemistry may include reaction with or without catalysts. Click chemistry for ex vivo or in vivo reactions provides a number of advantages over other reactions because each functional group is substantially inert against the chemical environment of the biological components used for tissue-engineering.

In embodiments, the present disclosure provides for polymer functionalization to immobilize chemotactic agent on the substrate by click chemistry so that it may be used to attract cells, modulate cell attachment, morphology, proliferation and/or differentiation to guarantee cell density and finally guide cellular ingrowth. This concept may be applied to tissue-engineered scaffolds and also to scaffolds used for stem cell therapy. In embodiments, the substrate may be formed in specific structure so that functionality is exposed as the substrate degrades to aid in guiding and orienting of cellular infiltration and ingrowths.

Methods of making such medical devices are described herein which include reacting a functionalized surface of the substrate with a chemotactic agent compound also having a functionalized portion. In embodiments, the surface of the substrate and the functionalized portion of the chemotactic agent are functionalized with reactive members involved in click chemistry.

In embodiments, a medical device may include a substrate having at least a portion thereof functionalized with at least one reactive member and a chemotactic agent functionalized with at least one complementary reactive member, wherein the at least one reactive member and the at least one complementary reactive member are covalently bonded, adhering the chemotactic agent to the substrate.

In embodiments, the substrate is formed from a polymer selected from the group consisting of polycarbonates, polyolefins, polymethacrylates, polystyrenes, polyamides, polyurethanes, polyethylene terephthalate, poly (lactic acid), poly (glycolic acid), poly(hydroxybutyrate), dioxanones (e.g., 1,4-dioxanone), δ-valerolactone, 1,dioxepanones (e.g., 1,4-dioxepan-2-one and 1,5-dioxepan-2-one), poly(phosphazine), polyesters, polyethylene glycol, polyethylene oxides, polyacrylamides, cellulose esters, fluoropolymers, vinyl polymers, silk, collagen, alginate, chitin, chitosan, hyaluronic acid, chondroitin sufate, polyhydroxyethylmethylacrylate, polyvinylpyrrolidone, polyvinyl alcohol, polyacrylic acid, polyacetate, polycaprolactone, polypropylene, glycerols, poly(amino acids), copoly (ether-esters), polyalkylene oxalates, polyamides, poly (iminocarbonates), polyalkylene oxalates, polyoxaesters, polyorthoesters, polyphosphazenes, polypeptides and copolymers, block copolymers, homoploymers, blends and combinations thereof.

In embodiments, the reactive member and the complementary reactive member bind to one another via a reaction selected from the group consisting of Huisgen cycloaddition reaction, a Diels-Alder reaction and a thiol-ene reaction. The Huisgen cycloaddition reaction may include an alkyne and an azide and is catalyzed by copper. The Huisgen cycloaddition reaction may involve a cyclooctyne reagent and an azide.

In embodiments, the reactive members and the complementary reactive members are thiols and alkenes.

In embodiments, the reactive members and the complementary reactive members are alkynes and azides. For example, the reactive member is an alkyne and the complementary reactive member is an azide. In embodiments, the reactive member is an azide and the complementary reactive member is an alkyne.

In embodiments, the reactive members and the complementary reactive members are dienes and alkenes.

In embodiments, the substrate is selected from the group consisting of a mesh, a patch, a scaffold, a suture, a ligature, a sling, a pellicle, a film, a barrier, and a foam.

In other embodiments, a method of manufacturing a medical device may include functionalizing a substrate to form a plurality of reactive members of a specific binding pair attached on a surface of the substrate, functionalizing at least one chemotactic agent to form a plurality of complementary reactive members of the specific binding pair, and contacting the substrate and the at least one chemotactic agent, wherein the plurality of reactive members and the plurality of complementary reactive member are covalently bonded, adhering the at least one chemotactic agent to the substrate.

In embodiments, the functionalizing of the substrate includes functionalizing the substrate with an azide. In embodiments, the functionalizing of the at least one chemotactic agent includes functionalizing the at least one chemotactic agent with an alkyne.

In further embodiments, a method of manufacturing a medical device may include contacting a functionalized substrate with a plurality of reactive members of a specific binding pair with at least one functionalized chemotactic agent with a plurality of complementary reactive members of the specific binding pair, wherein the plurality of reactive members and the plurality of complementary reactive member are covalently bonded, adhering the at least one functionalized chemotactic agent to the functionalized substrate. In embodiments, the method further comprises functionalizing the substrate with an azide. In embodiments, the method further comprises functionalizing the at least one chemotactic agent with an alkyne.

BRIEF DESCRIPTION OF THE DRAWINGS

The accompanying drawing, which is incorporated in and constitutes a part of this specification, illustrates embodiments of the disclosure and, together with a general description of the disclosure given above, and the detailed description of the embodiments given below, serves to explain the principles of the disclosure.

The FIGURE schematically illustrates a process for forming a medical device in accordance with an embodiment of the present disclosure.

DETAILED DESCRIPTION OF PREFERRED EMBODIMENTS

Implantable medical devices in accordance with the present disclosure include a substrate having a surface and a cellular growth promoting coating containing a chemotactic agent which is covalently bound to a surface of the substrate. At least a portion of a surface of the substrate is functionalized with a first reactive member and a portion of the chemotactic agent is functionalized with a second reactive member that is reactive with the first reactive member on the surface of the substrate. The first and second reactive members react to covalently bond the chemotactic agent to the surface of the substrate.

In embodiments, the surface of the substrate is functionalized with a first click-reactive member and the chemotactic agent is functionalized with a second click-reactive member complementary to the first click-reactive member. The "click-reactive members" are meant to include those reactive members used in the processes known to those skilled in the art as click chemistry.

Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

With reference to the FIGURE, a medical device is shown. The medical device includes a substrate shown as a three-dimensional tissue scaffold that promotes cell attachment and growth. In embodiments, the substrate of the medical devices described herein may be made from any polymer as discussed in further detail below. The polymer may be a homopolymer or a copolymer, including random copolymer, block copolymer, or graft copolymer. The polymer may be a linear polymer, a branched polymer, or a dendrimer. The polymer may be of natural or synthetic origin.

The substrate may be fabricated into any desired physical form. Some non-limiting examples include monofilaments, multifilaments, surgical meshes, ligatures, sutures, scaffolds, staples, patches, slings, foams, pellicles, films, barriers, and the like. The substrate may be fabricated for example, by spinning, casting, molding or any other fabrication technique known to those skilled in the art. The substrate may be made into any shape, such as, for example, a fiber, sheet, rod, staple, clip, needle, tube, foam, or any other configuration suitable for a medical device. Where the substrate is in the form of a fiber, the fiber may be formed into a textile using any known technique including, but not limited to, knitting, weaving, tatting and the like. It is further contemplated that the substrate may be a non-woven fibrous structure.

The chemostactic agent may be any chemoattractant or chemorepellents that induce chemotaxis within the cells surrounding the medical device. Suitable chemoattractants include, by way of example: glycyl-histidyl-lysine, alanyl-glycyl-seryl-glutamine, f-methionyl-leucyl-phenylalanine, glycyl-histidyl-glycine, and valinyl-glycyl-seryl-glutamine from Serva Fine Biochemicals, Garden City Park, N.Y.; collagen type I from Collagen Corp., Palo Alto, Calif.; epidermal growth factor from Collaborative Research, Waltham, Mass.; endotoxin standard, prostaglandin E, and histamine from Sigma Biochemicals, St. Louis, Mo., Tuftsin from Calbiochem, La Jolla, Calif., and heparin from Elkin-Sinn.

In order to covalently bond the chemotactic agent to the surface of the substrate, at least a portion of the surface of the substrate is functionalized with a first reactive member and a portion of the chemotactic agent is functionalized with a second reactive member. The first and second reactive members are complementary. By "complementary" it is meant that the first and second reactive members are able to specifically interact together to covalently bond the chemotactic agent to the functionalized polymer.

In embodiments, the surface of the substrate and the chemotactic agent are functionalized to include a first click-reactive member which is an alkyne and a second click-reactive member which is an azide, respectively. In embodiments, the surface of the substrate and the chemotactic agent are functionalized to include a first click-reactive member which is an azide and a second click-reactive member which is an alkyne, respectively. As those skilled in the art will recognize, reaction times between the azide and alkyne members can be reduced from about 24 hours at room temperature to mere seconds at room temperature by the presence of catalysts, such as transition metal ions (e.g., copper ions) as discussed in more detail below.

The first and second click-reactive members are intended to react and covalently bond the chemotactic agent to the functionalized surface of the substrate at a neutral pH. However, in some embodiments, the first and second click-reactive members may react quicker or more completely following the addition of a catalyst, including but not limited to, a pH modifier, a metal ion catalyst, such as transition metal ions (e.g., copper ions), or the introduction of heat or radiation, e.g., UV radiation, may enhance the formation of a covalent bond between the first and second click-reactive members.

The first and second reactive members may be positioned on the substrate and chemotactic agent using any variety of suitable chemical processes. With respect to the first reactive members on the substrate, it is contemplated that a plurality of first reactive members may be present and may be terminally located, or alternatively located along the length of the polymer chain.

In embodiments, the monomers from which the substrate is made can be functionalized so that the reactive members appear along the length of the polymer. The monomers can be initially functionalized with a member such as a halogen to provide a reactive site at which the desired first reactive member can be attached after polymerization. For example, the halogenated polymer can be reacted with sodium azide to provide azide groups along the polymer chain or with propagyl alcohol to provide alkyne groups along the polymer chain. Alternatively, a pre-formed polyester can be halogenated by reaction with a non-nucleophilic strong base, such as lithium diisopropylamide, followed by electrophilic substitution with iodine chloride. The halogenated polyester is then reacted with sodium azide or propagyl alcohol to provide azide or alkyne groups, respectively.

In embodiments, pendant functional groups can also be incorporated into the polymer backbone by, e.g., copolymerization with functionalized monomer such as lactones, cyclic carbonates and morpholine-2,5-diones. The azido group, $N_3$ is a nucleophilic group that exchanges with other nucleophilic groups, e.g., —OH, —$NH_2$ and halogens (Br, Cl, or I). For example, 1,3-dipolar compounds may be conjugated to aliphatic polyesters, by copolymerizing ϵ-caprolactone and α-chloro-ϵ-caprolactone and then substituting an azide group for the Cl atom. Polyesters can incorporate pendant dipolarophiles, e.g., propargyl groups, by copolymerization of ϵ-caprolactone and α-propargyl-δ-valerolactone. Copolymers of L-lactide containing propargyl groups may be prepared by ring opening copolymerization of 5-methyl-5-propargyloxy-carbonyl-1,3-dioxanone with L-lactide at a molar ratio of about 90:10 with $ZnEt_2$ as a catalyst as disclosed in Shi et al., Biomaterials, 29 (2008)1118-1126. Azide functionalized polystyrene is synthesized using atom transfer radical polymerization and subsequent modification with azidotrimethylsilane and tetrabutylammonium fluoride as disclosed in Dirks, et al., Chem. Comm., (2005) 4172-4174. Azides may be incorporated onto methacrylates, e.g., 3 azidopropyl methacrylate which is copolymerized to a block copolymer. Diels-Alder functionalities and thiol-ene functionalities are likewise incorporated into polymers herein.

In other embodiments, the substrate is functionalized after it has been fabricated into the desired form. For example, polymeric fibers can be functionalized after the spinning process. In embodiments, the fibers are surface treated and then activated with the first reactive member (optionally with a coupling agent, e.g., a silane coupling agent, being used). Surface activation of and biocompatible aliphatic polyesters can be achieved by acid or base hydrolysis, treatment by means of cold plasma, by chemical reactions or electromagnetic radiations. It is contemplated that such surface activation can be performed before or after the fibers are made into a textile structure.

Hydrolysis can be conducted in the presence of an aqueous solution of a base or an acid to accelerate surface reaction, inasmuch as excessively long processes of activation can induce a reduction in molecular weight and thus in the mechanical properties of the material. Suitable bases for obtaining watery solutions suited to the aim are, for example, strong alkalis, such as LiOH, $Ba(OH)_2$, $Mg(OH)_2$, NaOH, KOH, $Na_2CO_3$, $Ca(OH)_2$ and the weak bases, such as for example $NH_4OH$ and the ammines such as methylamine, ethylamine, diethylamine and dimethylamine. Acids suitable for surface hydrolysis treatments can be chosen, for example, from among HCl, $HClO_3$, $HClO_4$, $H_2SO_3$, $H_2SO_4$, $H_3PO_3$, $H_3PO_4$, HI, $HIO_3$, HBr, lactic acid, glicolic acid. Surface activation by means of hydrolysis can be conducted at temperatures preferably comprised between 0° C. and the material softening temperature. Plasma treatment can be carried out both in the presence of a reactive gas, for example air, Ar, $O_2$ with the formation of surface activation of oxygenate type, such as —OH, —CHO, —COOH.

Surface treatment, whether hydrolytic or with plasma, can remain unaltered or can be followed by further chemical modifications to provide the first reactive members on the substrate. Thus, for example, the COONa members generated by a base hydrolysis can be subsequently converted into COOH members by treatment with strong mineral acids. Further, the surface freeing of alcoholic members by means of a hydrolysis process can be followed by reaction by means of the addition of a compound provided with functional member or members able to react with surface alcoholic members, such as for example by means of the addition of an anhydride such as succinic anhydride, with the conversion of —OH members into —O—CO—$CH_2$—$CH_2$—COOH members. Suitable surface activation techniques are disclosed in U.S. Pat. No. 6,107,453, the entire disclosure of which is incorporated herein by this reference.

With respect to the chemotactic agent, it is contemplated that one or more than one second reactive members can be provided thereon. Chemotactic agent is provided with reactive members of a specific binding pair by conjugation to various components thereof. In one embodiment, the reactive members or complementary reactive members are attached directly to the chemotactic agent. In another embodiment, the reactive members or complementary reactive members are attached to the chemotactic agent via a linker. In either case, situating the reactive members or complementary reactive members on the chemotactic agent can be accomplished by suspending the reactive members or complementary reactive members in a solution or suspension and adding the chemotactic agent to the solution or suspension such that the reactive member binds thereto.

In embodiments, the surface of the substrate and the chemotactic agent are functionalized with electrophilic or nucleophilic functional members, such that, for example, a nucleophilic functional member on the surface of the substrate may react with an electrophilic functional member on the chemotactic agent to form a covalent bond.

Virtually any nucleophilic member can be used to functionalize the surface of the substrate, so long as reaction can occur with the electrophilic member on the chemotactic agent. Analogously, virtually any electrophilic member can be used to functionalize the chemotactic agent, so long as reaction can take place with the nucleophilic member on the surface of the substrate. In embodiments, the reactions of the complementary members may be complete in under 60 minutes, in embodiments under 30 minutes, in yet other embodiments, the reaction occurs in about 5 to 15 minutes or less.

Non-limiting examples of nucleophilic members include, but are not limited to, —$NH_2$, —NHR, —$N(R)_2$, —SH, —OH, —COOH, —$C_6H_4$—OH, —$PH_2$, —PHR, —$P(R)_2$, —NH—$NH_2$, —CO—NH—$NH_2$, —$C_5H_4N$, and the like, wherein R is hydrocarbyl, typically $C_1$-$C_4$ alkyl or monocyclic aryl. Organometallic moieties are also useful nucleophilic members for the purposes of this disclosure, particularly those that act as carbanion donors. Examples of organometallic moieties include: Grignard functionalities —RMgHal wherein R is a carbon atom (substituted or unsubstituted), and Hal is halo, typically bromo, iodo or chloro; and lithium-containing functionalities, typically alkyllithium members; sodium-containing functionalities.

It will be appreciated by those of ordinary skill in the art that certain nucleophilic members may be activated with a base so as to be capable of reaction with an electrophile. In embodiments, when there are nucleophilic sulfhydryl and hydroxyl members on the surface of the substrate, the composition may be admixed with an aqueous base in order to remove a proton and provide an —$S^-$ or —$O^-$ species to enable reaction with an electrophile. Unless it is desirable for the base to participate in the reaction, a non-nucleophilic base is used. In some embodiments, the base may be present as a component of a buffer solution.

The selection of electrophilic members provided on the chemotactic agent is made so that reaction is possible with the specific nucleophilic members on the surface of the substrate. Thus, when the surface of the substrate is functionalized with amino members, the chemotactic agent is functionalized with members selected so as to react with amino members. Analogously, when the surface of the substrate is functionalized with sulhydryl moieties, the corresponding electrophilic members are sulfhydryl-reactive members, and the like.

By way of example, when the surface of the substrate is functionalized with amino members (generally although not necessarily primary amino members), the electrophilic members present on the chemotactic agent are amino reactive members such as, but not limited to: carboxylic acid esters, including cyclic esters and "activated" esters; acid chloride members (—CO—Cl); anhydrides (—(CO)—O—(CO)—R); ketones and aldehydes, including α,β-unsaturated aldehydes and ketones such as —CH=CH—CH=O and —CH=CH—$C(CH_3)$=O; (5) halides; isocyanate (—N=C=O); isothiocyanate (—N=C=S); epoxides; activated hydroxyl members (e.g., activated with conventional activating agents such as carbonyldiimidazole or sulfonyl chloride); and olefins, including conjugated olefins, such as ethenesulfonyl (—$SO_2CH$=$CH_2$) and analogous functional members, including acrylate (—$CO_2$—C=$CH_2$), methacrylate (—$CO_2$—$C(CH_3)$=$CH_2$)), ethyl acrylate (—$CO_2$—C($CH_2CH_3$)=$CH_2$), and ethyleneimino (—CH=CH—C=NH). Since a carboxylic acid member is not susceptible to react with a nucleophilic amine, components containing carboxylic acid members must be activated so as to be amine-reactive. Activation may be accomplished in a variety of ways, such as reaction with a suitable hydroxyl-containing compound in the presence of a dehydrating agent such as dicyclohexylcarbodiimide (DCC) or dicyclohexylurea (DHU). A carboxylic acid can be reacted with an alkoxy-substituted N-hydroxy-succinimide or N-hydroxysulfosuccinimide in the presence of DCC to form reactive electrophilic members, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride member. In a further example, a carboxylic acid may be converted to an acid chloride member using, e.g., thionyl chloride or an acyl chloride capable of an exchange reaction. Specific reagents and procedures used to carry out such activation reactions will be known to those of ordinary skill in the art and are described in the pertinent texts and literature.

Analogously, when the surface of the substrate is functionalized with sulfhydryl, the electrophilic members present on the chemotactic agent are members that react with a sulfhydryl moiety. Such reactive members include those that form thioester linkages upon reaction with a sulfhydryl member, such as those described in PCT Publication No. WO 00/62827 to Wallace et al., entire disclosure of which is incorporated herein by reference. As explained in detail therein, such "sulfhydryl reactive" members include, but are not limited to: mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarinide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates. With these sulfhydryl reactive members, auxiliary reagents can also be used to facilitate bond formation, e.g., 1-ethyl-3-[3-dimethylaminopropyl]carbodiimide can be used to facilitate coupling of sulfhydryl members to carboxyl-containing members.

In addition to the sulfhydryl reactive members that form thioester linkages, various other sulfydryl reactive functionalities can be utilized that form other types of linkages. For example, compounds that contain methyl imidate derivatives form imido-thioester linkages with sulfhydryl members. Alternatively, sulthydryl reactive members can be employed that form disulfide bonds with sulthydryl members, such members generally have the structure —S—S—Ar where Ar is a substituted or unsubstituted nitrogen-containing heteroaromatic moiety or a non-heterocyclic aromatic member substituted with an electron-withdrawing moiety, such that Ar may be, for example, 4-pyridinyl, o-nitrophenyl, m-nitrophenyl, p-nitrophenyl, 2,4-dinitrophenyl, 2-nitro-4-benzoic acid, 2-nitro-4-pyridinyl, etc. In such instances, auxiliary reagents, i.e., mild oxidizing agents such as hydrogen peroxide, can be used to facilitate disulfide bond formation.

Yet another class of sulfhydryl reactive members forms thioether bonds with sulfhydryl members. Such members include, inter alia, maleimido, substituted maleimido, haloalkyl, epoxy, imino, and aziridino, as well as olefins (including conjugated olefins) such as ethenesulfonyl, etheneimino, acrylate, methacrylate, and α,β-unsaturated aldehydes and ketones.

When the surface of the substrate is functionalized with —OH, the electrophilic functional members on the chemotactic agent must react with hydroxyl members. The hydroxyl member may be activated as described above with respect to carboxylic acid members, or it may react directly in the presence of base with a sufficiently reactive electrophile such as an epoxide member, an aziridine member, an acyl halide, an anhydride, and the like. When the surface of the substrate is functionalized with an organometallic nucleophile such as a Grignard functionality or an alkyllithium member, suitable electrophilic functional members for reaction therewith are those containing carbonyl members, including, by way of example, ketones and aldehydes.

It will also be appreciated that certain functional members can react as nucleophiles or as electrophiles, depending on the selected reaction partner and/or the reaction conditions. For example, a carboxylic acid member can act as a nucleophile in the presence of a fairly strong base, but generally acts as an electrophile allowing nucleophilic attack at the carbonyl carbon and concomitant replacement of the hydroxyl member with the incoming nucleophile.

Table 1, below illustrates, solely by way of example, representative complementary pairs of electrophilic and nucleophilic functional members that may be employed in functionalizing the substrate (e.g., $R_1$ in Table 1) and the chemotactic agent (e.g., $R_2$ in Table 1).

TABLE 1

| REPRESENTATIVE NUCLEOPHILIC COMPONENT (A, $FN_{NU}$) | REPRESENTATIVE ELECTROPHILIC COMPONENT (B, $FN_{EL}$) | RESULTING LINKAGE |
|---|---|---|
| $R^1$—$NH_2$ | $R^2$—O—(CO)—O—N—($COCH_2$) (succinimidyl carbonate terminus) | $R^1$—NH—(CO)—O—$R^2$ |
| $R^1$—SH | $R^2$—O—(CO)—O—N—($COCH_2$) | $R^1$—S—(CO)—O—$R^2$ |
| $R^1$—OH | $R^2$—O—(CO)—O—N—($COCH_2$) | $R^1$—S—(CO)—$R^2$ |
| $R^1$—$NH_2$ | $R^2$—O(CO)—CH=$CH_2$ (acrylate terminus) | $R^1$—NH—$CH_2CH_2$—(CO)—O—$R^2$ |
| $R^1$—SH | $R^2$—O—(CO)—CH=$CH_2$ | $R^1$—S—$CH_2CH_2$—(CO)—O—$R^2$ |
| $R^1$—OH | $R^2$—O—(CO)—CH=$CH_2$ | $R^1$—O—$CH_2CH_2$—(CO)—O—$R^2$ |
| $R^1$—$NH_2$ | $R^2$—O(CO)—$(CH_2)_3$—$CO_2N(COCH_2)$ (succinimidyl glutarate terminus) | $R^1$—NH—(CO)—$(CH_2)_3$—(CO)—$OR^2$ |
| $R^1$—SH | $R^2$—O(CO)—$(CH_2)_3$—$CO_2$—N($COCH_2$) | $R^1$—S—(CO)—$(CH_2)_3$—(CO)—$OR^2$ |
| $R^1$—OH | $R^2$—O(CO)—$(CH_2)_3$—$CO_2$—N($COCH_2$) | $R^1$—O—(CO)—$(CH_2)_3$—(CO)—$OR^2$ |
| $R^1$—$NH_2$ | $R^2$—O—$CH_2$—$CO_2$—N($COCH_2$) (succinimidyl acetate terminus) | $R^1$—NH—(CO)—$CH_2$—$OR^2$ |
| $R^1$—SH | $R^2$—O—$CH_2$—$CO_2$—N($COCH_2$) | $R^1$—S—(CO)—$CH_2$—$OR^2$ |
| $R^1$—OH | $R^2$—O—$CH_2$—$CO_2$—N($COCH_2$) | $R^1$—O—(CO)—$CH_2$—$OR^2$ |
| $R^1$—$NH_2$ | $R^2$—O—NH(CO)—$(CH_2)_2$—$CO_2$—N($COCH_2$) (succinimidyl succinamide terminus) | $R^1$—NH—(CO)—$(CH_2)_2$—(CO)—NH—$OR^2$ |
| $R^1$—SH | $R^2$—O—NH(CO)—$(CH_2)_2$—$CO_2$—N($COCH_2$) | $R^1$—S—(CO)—$(CH_2)_2$—(CO)—NH—$OR^2$ |
| $R^1$—OH | $R^2$—O—NH(CO)—$(CH_2)_2$—$CO_2$—N($COCH_2$) | $R^1$—O—(CO)—$(CH_2)_2$—(CO)—NH—$OR^2$ |
| $R^1$—$NH_2$ | $R^2$—O—$(CH_2)_2$—CHO (propionaldehyde terminus) | $R^1$—NH—(CO)—$(CH_2)_2$—$OR^2$ |
| $R^1$—$NH_2$ | $R^2$—O—$CH_2$—CH(—O—)$CH_2$ (glycidyl ether terminus) | $R^1$—NH—$CH_2$—CH(OH)—$CH_2$—$OR^2$ and $R^1$—N[$CH_2$—CH(OH)—$CH_2$—$OR^2$]$_2$ |
| $R^1$—$NH_2$ | $R^2$—O—$(CH_2)_2$—N=C=O (isocyanate terminus) | $R^1$—NH—(CO)—NH—$CH_2$—$OR^2$ |
| $R^1$—$NH_2$ | $R^2$—$SO_2$—CH=$CH_2$ (vinyl sulfone terminus) | $R^1$—NH—$CH_2CH_2$—$SO_2$—$R^2$ |
| $R^1$—SH | $R^2$—$SO_2$—CH=$CH_2$ | $R^1$—S—$CH_2CH_2$—$SO_2$—$R^2$ |

In embodiments, Huisgen cycloaddition may also be used in click chemistry. Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is a variant of the Huisgen 1,3-dipolar cycloaddition reaction between alkyl-aryly-sulfonyl azides, C—N triple bonds and C—C triple bonds which is well-suited herein. The results of these reactions are 1,2 oxazoles, 1,2,3 triazoles or tetrazoles. 1,2,3 Triazoles may be formed by a copper catalyzed Huisgen reaction between alkynes and alkyl/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, are especially well-suited for use herein due to low toxicity since substituted cyclooctyne possess ring strain and electron-withdrawing substituents such as fluorine, that together promote a [3+2] dipolar cycloaddition with azides. Suitable examples of substituted cycloctyne include difluorinated cyclooctyne and 6,7-dimethoxyazacyclooct-4-yne. Reaction of the alkynes and azides is very specific and essentially inert against the chemical environment of biological tissues. One reaction scheme may be represented as:

a)

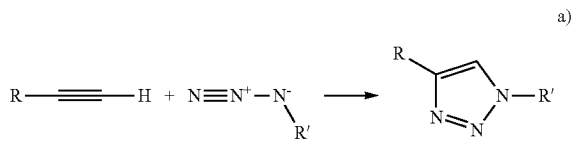

where R and R' are a substrate or a chemotactic agent.

In accordance with the disclosure herein, a medical device, such as a surgical patch or mesh is provided with a plurality of reactive members of a specific binding pair attached on the surface of the medical device. When the reactive members of the medical device are contacted with the chemotactic agent containing complementary reactive members of the specific binding pair, covalent attachment occurs, thus adhering the device to the chemotactic agent. In embodiments, the reactive members may be either a dipolarophile or a 1,3 dipolar compound depending on which complement is applied to the chemotactic agent or the medical device. For example, if a dipolarophile is located on the device, the 1,3 dipolar compound will be located on the chemotactic agent. If a dipolarophile is located on the chemotactic agent, the 1,3 dipolar compound will be located on the device. In embodiments, the Diels-Alder members of a specific binding pair may be either a diene and a dienophile depending on which complement is applied to the chemotactic agent or the medical device. For example, if a diene is located on the device, the dienophile can be located on the chemotactic agent. If a diene is located on the chemotactic agent, the dienophile can be located on the device. In embodiments, the thiol-ene members of a specific binding pair may be either a thiol and an alkene depending on which complement is applied to the chemotactic agent or the device. For example, if a thiol is located on the device, the alkene can be located on the chemotactic agent. If a thiol is located on the chemotactic agent, the alkene can be located on the device.

In embodiments, Diels-Alder reaction may also be used in click chemistry. The Diels-Alder reaction combines a diene (a molecule with two alternating double bonds) and a dienophile (an alkene) to make rings and bicyclic compounds. Examples include:

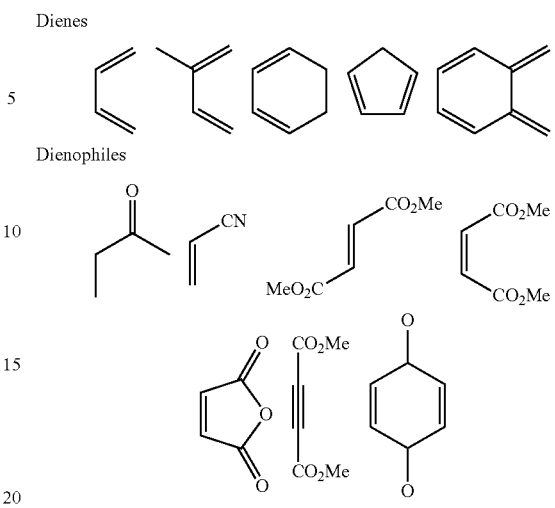

The thiol-alkene (thiol-ene) reaction is a hydrothiolation, i.e., addition of RS—H across a C═C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

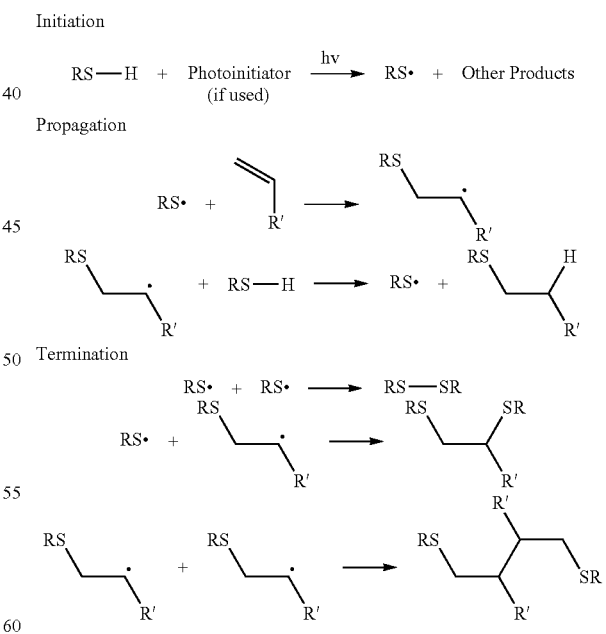

The substrate may be constructed from any biocompatible synthetic or natural materials, including absorbable polymers or biocompatible non-absorbable polymers. Examples of suitable polymers include polycarbonates; polyolefins such as polyethylene, including ultra high molecular weight polyethylene, (UHMWPE); polymethacrylates; polystyrenes;

polyamides; polyurethanes; polyethylene terephthalate; poly (lactic acid); poly(glycolic acid); poly(hydroxbutyrate); dioxanones (e.g., 1,4-dioxanone); δ-valerolactone; 1,dioxepanones, such as 1,4-dioxepan-2-one and 1,5-dioxepan-2-one; poly(phosphazine); polyesters such as polyethylene terepthhalate (PET), polyethylene glycol, polyethylene oxides; polyacrylamides; fluorinated polymers such as fluoroethylenes, propylenes, fluoroPEGs, polytetrafluoroethylene; vinyl polymers; natural biological polymers, which may be non-oxidized or oxidized, including but not limited to silk, collagen, gelatin, cellulose, hydroxypropyl cellulose, carboxyethyl cellulose, cellulose esters, alginate, chitin, chitosan, hyaluronic acid, chondroitin sulfate, glycosaminoglycans; polyhydroxyethylmethylacrylate; polyvinylpyrrolidone; polyvinyl alcohol; polyacrylic acid; polyacetate; polycaprolactone; polypropylene; glycerols; poly(amino acids); copoly(ether-esters); polyalkylene oxalates; polyamides; poly(iminocarbonates); polyalkylene oxalates; polyoxaesters; polyorthoesters; polyphosphazenes; nylons; silicones; polybutesters; polyaryletherketone; as well as polypeptides, copolymers, block copolymers, homoploymers, blends and combinations thereof.

In the present application, the term "bioresorbable" and "bioabsorbable" are used interchangeably and are intended to mean the characteristic according to which an implant and/or a material is resorbed by the biological tissues and the surrounding fluids and disappears in vivo after a given period of time, that may vary, for example, from one day to several months, depending on the chemical nature of the implant and/or of the material. Non bioresorbable material—also called permanent material—is not substantially resorbed by tissues and surrounding fluids, after 2 years and more, keeping in particular most (e.g., >80%) of their mechanical properties after such a time. The term "biocompatible" is intended to mean the characteristic according to which an implant and/or a material is well-integrated by the biological tissues and the surrounding fluids without inducing excessive inflammation reaction around the bulk of the material or due to its degradation. The material should avoid also the formation of a fibrous capsule which usually results in the delay of the cellular integration of a porous implant.

In embodiments, the medical device may be a surgical patch. The surgical patch may be selected from any conventional patch type that is suitable for use in tissue reinforcement, e.g., hernia repair, or as an anti-adhesion barrier, hemostatic patch, bandages, pledgets and the like. Many types of patches are currently available and are well known to those skilled in the art. Exemplary polymeric patch materials include nonabsorbable polyester cloth, polyester sheeting, acrylic cloth, polyvinyl sponge or foam, polytetrafluroethylene (PTFE), expanded PTFE, and polyvinyl cloth. Any of the biocompatible polymers listed above may be utilized. In another embodiment, the medical device is a surgical mesh, e.g., polypropylene mesh, nylon mesh, and Dacron mesh. Exemplary absorbable meshes include collagen, polyglycolic acid, polyglactin, polycaprolactone, chitosan, and carbon fiber mesh. It should be understood that any of the above-mentioned biocompatible polymers may be suitable for use herein.

The patch or mesh may be produced from fibers of any biocompatible polymer using any techniques known to those skilled in the art, such as knitting, weaving, tatting, nonwoven techniques, freeze drying, solvent casting and the like. It is envisioned that the patch or mesh may be formed from any permanent biocompatible materials (e.g. polyesters, polypropylene), biodegradable biocompatible materials (e.g. polylactic acid, polyglycolic acid, oxidized cellulose, and chitosan) or with a combination at any proportion of both permanent and biodegradable materials as well as biocompatible polymers listed above. The medical device may, for example, have an openwork three-dimensional ("3D") structure as disclosed in U.S. Pat. No. 6,451,032, the entire disclosure of which is incorporated herein by reference, e.g., a "honeycomb" structure, and thus a certain thickness which separates the two surfaces of the fabric.

In embodiments, the patch may be formed from a biopolymer foam having openings or pores over at least a portion of a surface thereof. The pores may be in sufficient number and size so as to interconnect across the entire thickness of the porous layer. Alternatively, the pores may not interconnect across the entire thickness of the porous layer. Closed cell foams are illustrative examples of structures in which the pores may not interconnect across the entire thickness of the porous layer. In embodiments, the pores may not extend across the entire thickness of the foam, but rather are present at a portion of the surface thereof. In some embodiments, the openings or pores may be disposed on a portion of the surface of the porous layer, with other portions of the porous layer having a non-porous texture. Those skilled in the art may envision other pore distribution patterns and configurations for the foam.

In embodiments, the foam may be made from non-denatured collagen or collagen which has at least partially lost its helical structure through heating or any other known method, consisting mainly of non-hydrolyzed α chains, and having a molecular weight, in embodiments, of about 100 kDa. The collagen may be native collagen or atelocollagen, which may be obtained via pepsin digestion and/or after moderate heating as defined hereinabove. The collagen may be cured to any desired degree.

Various modifications and variations of the polymers, chemotactic agents, medical devices, click-reactive members and processes described herein will be apparent to those skilled in the art from the foregoing detailed description. Such modifications and variations are intended to come within the scope of the following claims.

What is claimed is:
1. A medical device comprising:
   a substrate having a surface functionalized with at least one click reactive member; and
   a chemotactic agent functionalized with at least one complementary click reactive member, wherein the at least one click reactive member and the at least one complementary click reactive member are covalently bonded, adhering the chemotactic agent directly to the surface of the substrate, and the surface of the substrate promotes cellular integration.
2. The medical device according to claim 1, wherein the substrate is formed from a polymer selected from the group consisting of polycarbonates, polyolefins, polymethacrylates, polystyrenes, polyamides, polyurethanes, polyethylene terephthalate, poly (lactic acid), poly (glycolic acid), poly (hydroxbutyrate), dioxanones, δ-valerolactone, 1,dioxepanones, poly (phosphazine), polyesters, polyethylene glycol, polyethylene oxides, polyacrylamides, cellulose esters, fluoropolymers, vinyl polymers, silk, collagen, alginate, chitin, chitosan, hyaluronic acid, chondroitin sulfate, polyhydroxyethylmethylacrylate, polyvinylpyrrolidone, polyvinyl alcohol, polyacrylic acid, polyacetate, polycaprolactone, polypropylene, glycerols, poly(amino acids), copoly (ether-esters), polyalkylene oxalates, polyamides, poly (iminocarbonates), polyalkylene oxalates, polyoxaesters, polyorthoe- sters, polyphosphazenes, polypeptides and copolymers, block copolymers, homoploymers, blends and combinations thereof.

3. The medical device according to claim 1, wherein the at least one click reactive member and the at least one complementary click reactive member bind to one another via a reaction selected from the group consisting of Huisgen cycloaddition reaction, a Diels-Alder reaction and a thiol-ene reaction.

4. The medical device according to claim 3, wherein the Huisgen cycloaddition reaction includes an alkyne and an azide and is catalyzed by copper.

5. The medical device according to claim 3, wherein the Huisgen cycloaddition reaction involves a cyclooctyne reagent and an azide.

6. The medical device according to claim 3, wherein the at least one click reactive member and the at least one complementary click reactive member are thiols and alkenes.

7. The medical device according to claim 3, wherein the at least one click reactive member and the at least one complementary click reactive member are alkynes and azides.

8. The medical device according to claim 7, wherein the at least one click reactive member is an alkyne and the at least one complementary click reactive member is an azide.

9. The medical device according to claim 7, wherein the at least one click reactive member is an azide and the at least one complementary click reactive member is an alkyne.

10. The medical device according to claim 3, wherein the at least one click reactive member and the at least one complementary click reactive member are dienes and alkenes.

11. The medical device according to claim 1, wherein the substrate is selected from the group consisting of a mesh, a patch, a scaffold, a suture, a ligature, a sling, a pellicle, a film, a barrier, and a foam.

12. A method of manufacturing a medical device, the method comprising:
    functionalizing a substrate to form a plurality of click reactive members of a specific binding pair attached on a surface of the substrate;
    functionalizing at least one chemotactic agent to form a plurality of complementary click reactive members of the specific binding pair; and
    contacting the substrate and the at least one chemotactic agent, wherein the plurality of click reactive members and the plurality of complementary click reactive member are covalently bonded, adhering the at least one chemotactic agent directly to the surface of the substrate, and the surface of the substrate promotes cellular integration.

13. The method according to claim 12, wherein the functionalizing of the substrate includes functionalizing the substrate with an azide.

14. The method according to claim 13, wherein the functionalizing of the at least one chemotactic agent includes functionalizing the at least one chemotactic agent with an alkyne.

15. A method of manufacturing a medical device, the method comprising:
    contacting a functionalized surface of a substrate with a plurality of click reactive members of a specific binding pair with at least one functionalized chemotactic agent with a plurality of complementary click reactive members of the specific binding pair, wherein the plurality of click reactive members and the plurality of complementary click reactive member are covalently bonded, adhering the at least one functionalized chemotactic agent directly to the functionalized surface of the substrate, and the surface of the substrate promotes cellular integration.

16. The method according to claim 15, further comprising functionalizing the substrate with an azide.

17. The method according to claim 16, further comprising functionalizing the at least one chemotactic agent with an alkyne.

18. The medical device according to claim 1, wherein the at least one chemotactic agent is selected from the group consisting of glycyl-histidyl-lysine, alanyl-glycyl-seryl-glutamine, f-methionyl-leucyl-phenylalanine, glycyl-histidyl-glycine, valinyl-glycyl-seryl-glutamine, and Tuftsin.

19. The method according to claim 12, wherein the at least one chemotactic agent is selected from the group consisting of glycyl-histidyl-lysine, alanyl-glycyl-seryl-glutamine, f-methionyl-leucyl-phenylalanine, glycyl-histidyl-glycine, valinyl-glycyl-seryl-glutamine, and Tuftsin.

20. The method according to claim 15, wherein the at least one functionalized chemotactic agent is selected from the group consisting of glycyl-histidyl-lysine, alanyl-glycyl-seryl-glutamine, f-methionyl-leucyl-phenylalanine, glycyl-histidyl-glycine, valinyl-glycyl-seryl-glutamine, and Tuftsin.

* * * * *